(12) United States Patent
Green et al.

(10) Patent No.: US 10,328,464 B2
(45) Date of Patent: Jun. 25, 2019

(54) METHOD AND APPARATUS FOR SORTING HETEROGENEOUS MATERIAL

(71) Applicant: JJG IP Holdings, LLC, Hampstead, NH (US)

(72) Inventors: John F. Green, Baldwinsville, NY (US); Peter A. Mendre, Haverhill, MA (US)

(73) Assignee: JJG IP Holdings LLC, Hampstead, NH (US)

( * ) Notice: Subject to any disclaimer, the term of this patent is extended or adjusted under 35 U.S.C. 154(b) by 0 days.

(21) Appl. No.: 15/921,766

(22) Filed: Mar. 15, 2018

(65) Prior Publication Data

US 2018/0200762 A1    Jul. 19, 2018

Related U.S. Application Data

(63) Continuation of application No. 14/259,584, filed on Apr. 23, 2014, now Pat. No. 9,950,346, which is a continuation of application No. 12/620,909, filed on Nov. 18, 2009, now abandoned.

(60) Provisional application No. 61/115,771, filed on Nov. 18, 2008.

(51) Int. Cl.
| | |
|---|---|
| *B07C 5/34* | (2006.01) |
| *A61K 9/00* | (2006.01) |
| *A61K 31/498* | (2006.01) |
| *A61K 47/10* | (2017.01) |
| *A61K 47/18* | (2017.01) |
| *A61K 47/32* | (2006.01) |
| *A61K 47/38* | (2006.01) |
| *C07D 403/12* | (2006.01) |
| *C07C 51/41* | (2006.01) |
| *C07C 65/11* | (2006.01) |

(52) U.S. Cl.
CPC .............. *B07C 5/34* (2013.01); *A61K 9/0019* (2013.01); *A61K 31/498* (2013.01); *A61K 47/10* (2013.01); *A61K 47/183* (2013.01); *A61K 47/32* (2013.01); *A61K 47/38* (2013.01); *C07C 51/41* (2013.01); *C07C 65/11* (2013.01); *C07D 403/12* (2013.01)

(58) Field of Classification Search
USPC ....................................................... 700/223
See application file for complete search history.

(56) References Cited

U.S. PATENT DOCUMENTS

| | | | | |
|---|---|---|---|---|
| 3,802,558 A * | 4/1974 | Rhys | .................... | B07C 5/02 209/557 |
| 5,848,706 A * | 12/1998 | Harris | .................... | B07C 5/342 209/580 |
| 5,862,919 A * | 1/1999 | Eason | .................... | B07C 5/00 209/577 |
| 2002/0135760 A1* | 9/2002 | Poole | .................... | G01N 21/31 356/300 |
| 2003/0132402 A1* | 7/2003 | Holl | .................... | G06K 9/2036 250/556 |

(Continued)

*Primary Examiner* — Kyle O Logan

(74) *Attorney, Agent, or Firm* — Maine Cernota & Rardin

(57) ABSTRACT

A system is provided for the identification and separation of heterogeneous material, the system comprising: a hyperspectral identification system for capturing spectra of material; a computer receiving and analyzing data from the hyperspectral identification system and selecting desired materials from the heterogeneous materials; and an ejection system, whereby the desired materials are ejected from the system.

15 Claims, 7 Drawing Sheets

(56) References Cited

U.S. PATENT DOCUMENTS

| | | | |
|---|---|---|---|
| 2005/0212200 A1* | 9/2005 | Van Nice | B65H 29/60 271/265.04 |
| 2007/0029232 A1* | 2/2007 | Cowling | B07C 5/3425 209/577 |
| 2007/0029233 A1* | 2/2007 | Reinhold | B07C 5/3416 209/578 |
| 2007/0278139 A1* | 12/2007 | Cowling | B07C 5/36 209/606 |
| 2008/0257793 A1* | 10/2008 | Valerio | B07C 5/3416 209/567 |

* cited by examiner

METHOD AND APPARATUS FOR SORTING HETEROGENEOUS MATERIAL

RELATED APPLICATIONS

This application is a continuation of U.S. application Ser. No. 14/259,584, filed on Apr. 23, 2014, which is a continuation of U.S. application Ser. No. 12/620,909, filed on Nov. 18, 2009. U.S. application Ser. No. 12/620,909 claims the benefit of U.S. Provisional Application No. 61/115,771, filed Nov. 18, 2008. These applications are herein incorporated by reference in their entirety for all purposes.

FIELD OF THE INVENTION

The invention relates to methods and apparatus for sorting heterogeneous material, and more particularly, to an automatic sorting systems for the identification and separation of such material.

BACKGROUND OF THE INVENTION

Recycling of post consumer and industrial material requires that composite materials be sorted and separated according to color, composition, shape, size, or any of several criteria. Such sorting has traditionally been done manually, wherein sorters visually identify objects to be sorted, and transfer them from one conveyer belt to another running parallel to the first. This is labor intensive and expensive. Automated systems have been developed to replace this traditional hand sorting. In such systems, materials are identified by conventional optical scanner and are transferred from a first conveyer by means of a mechanical or pneumatic force to a second conveyer. Such systems typically are imprecise in their sorting, allowing materials to be mixed, which must then be resorted before pelletization. This lack of precision is due both to the optical scanning mechanism, and the imprecise mechanical and pneumatic sorting mechanism.

Known optical sorting techniques carry materials on a conveyor or vibratory deck and then rely on air jet propulsion methods and or finger push methods that lift or push desired picked materials past an outboard barrier. Unselected items typically fall off the end of the optics conveyor or shaker deck and often dropped on a conveyor below that would transport that material to another optical system where the process occurs again. The selected ejected items that have been propelled either land on another belt or vibratory conveyor and deposited in a holding bunker often with some type of post sorting to qualify the material is correctly identified. Such a system requires extensive room, both horizontally and vertically to allow for conveyers and dropping of the materials.

What is needed therefore is a means for automated sorting heterogeneous material with high degrees of precision.

SUMMARY OF THE INVENTION

One embodiment of the present invention provides a system for the identification and sorting of heterogeneous material, the system comprising: a hyperspectral identification system for capturing spectra of material, the hyperspectral identification system comprises at least one hyperspectral camera the hyperspectral camera receiving a plurality of selected spectral bands of infrared and visible light corresponding to spectral signatures of target materials to be identified if present in the heterogeneous material; the camera disposed proximate to a visible or infrared light source, the light source and the at least one hyperspectral camera are disposed on the same side of a stream of the heterogeneous material; a solid belt having first and second ends, the belt running beneath the hyperspectral identification system and upon which the heterogeneous material is conveyed from the first end to the second end, the belt traveling at a preset rate, the hyperspectral identification system being disposed over the second end of the belt; a computer receiving and analyzing data from the hyperspectral identification system and selecting materials of a first user defined category from the materials; and an ejection system disposed immediately after the second end of the belt, whereby the desired materials are separated from the heterogeneous material, the ejection system being triggered by the computer at a preset time delay equal to the distance between the camera and the ejection system divided by the rate of travel of the belt.

A further embodiment of the present invention provides such a system further comprising a conveyer to deliver the heterogeneous material to the system.

Yet another embodiment of the present invention provides such a system further comprising a receiving system, whereby the materials of a first user defined category are segregated and collected.

A yet further embodiment of the present invention provides such a system further comprising an array of lights disposed proximate to the hyperspectral identification system.

Even another embodiment of the present invention provides such a system wherein the lights have a wavelength suitable for hyperspectral imaging.

An even further embodiment of the present invention provides such a system wherein the hyperspectral identification system is configured to collect spectral and spatial information from heterogeneous material entering the system, store the spectral and spatial information as images.

Still another embodiment of the present invention provides such a system wherein the computer comprises software configured to compare the images to images stored in a library of images.

A still further embodiment of the present invention provides such a system wherein the ejection system comprises a plurality of independently controlled air nozzles disposed beneath the material, and a blower hood disposed above the material, the blower hood providing a air current whereby the selected material is blown out of a discharge port.

Yet another embodiment of the present invention provides such a system wherein the heterogeneous materials comprise waste and recyclable materials.

A yet further embodiment of the present invention provides such a system wherein the computer can select a plurality of user defined materials.

Still yet another embodiment of the present invention provides such a system wherein the ejection system comprises a mechanical ejector.

A still yet further embodiment of the present invention provides such a system wherein the ejection system comprises a fluid jet.

Still even another embodiment of the present invention provides such a system wherein the fluid jet is a water jet.

One embodiment of the present invention provides a method for sorting heterogeneous material, the method comprising: reflecting visible or infrared light from the surface of the heterogeneous material disposed on a conveyer; conveying the heterogeneous material at a predetermined rate through a hyperspectral imager; generating hyperspectral images of the heterogeneous material by receiving a plurality of selected spectral bands of infrared and visible light corresponding to spectral signatures of target materials to be identified if present in the heterogeneous material as the heterogeneous material passes on the conveyer beneath the hyperspectral imaginer; comparing the hyperspectral images of the heterogeneous material to hyperspectral images of known materials; identifying the target materials; after a preset time interval from the identifying the target material, the interval equal to the distance between the hyperspectral imager and a separating system divided by the predetermined rate, physically isolating target material from the heterogeneous material by separating the selected material from the heterogeneous material as it leaves the conveyer immediately after the hyperspectral imager.

Another embodiment of the present invention provides such a method further comprising illuminating the heterogeneous material to optimize the hyperspectral images.

A further embodiment of the present invention provides such a method wherein the hyperspectral images comprise spectral and spatial data for articles within the heterogeneous material.

Even another embodiment of the present invention provides such a method wherein the heterogeneous material comprises waste material and recyclable material in combination.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

In one embodiment of the present invention, a system is provided having a hyperspectral identification system and a positively sorted air ejector.

Figure 1:
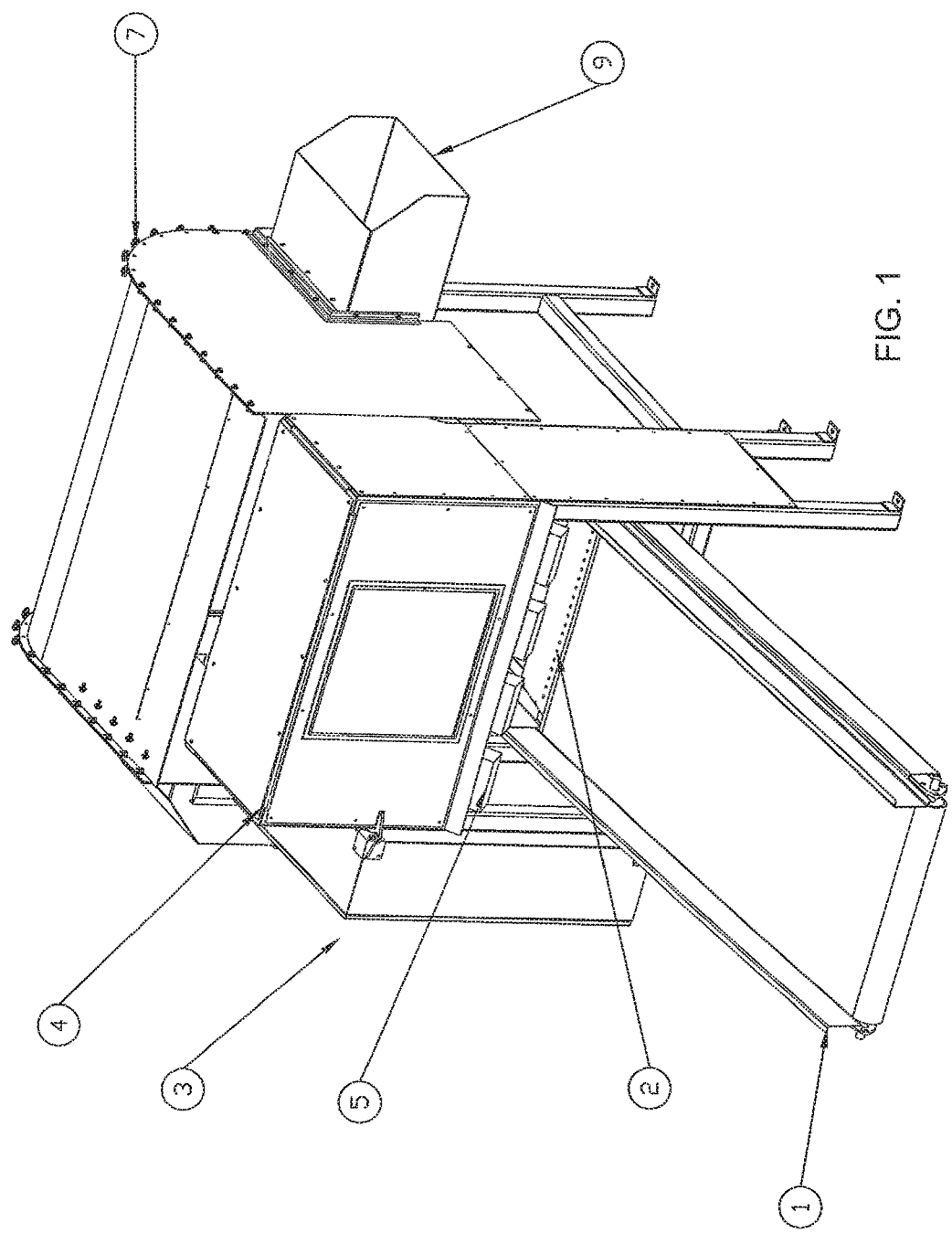
FIG. 1 is a front perspective drawing illustrating a system for the separation of heterogeneous material configured in accordance with one embodiment of the present invention.
Figure 2:
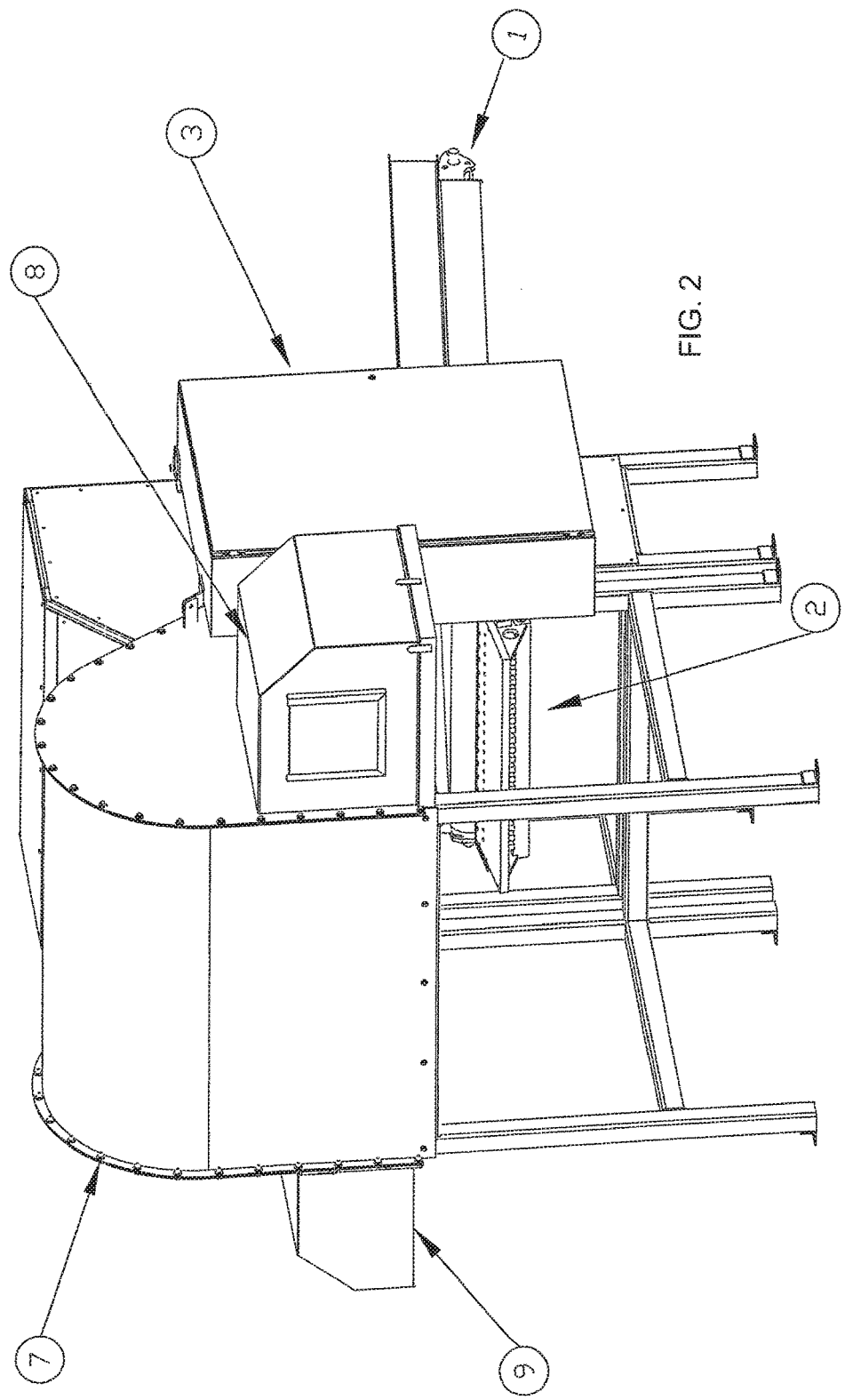
FIG. 2 is a rear perspective drawing illustrating a system for the separation of heterogeneous material configured in accordance with one embodiment of the present invention.
Figure 3:
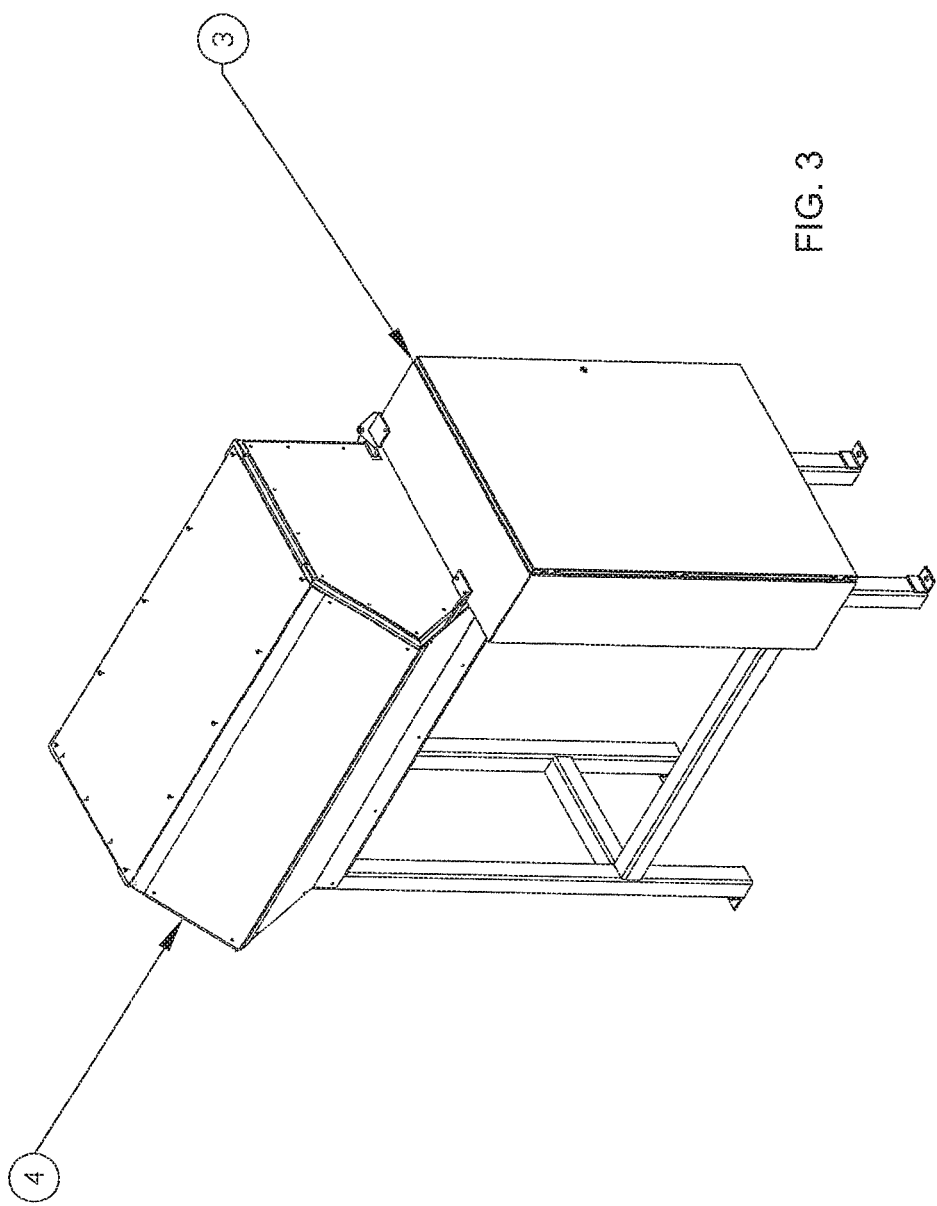
FIG. 3 is a rear perspective drawing illustrating an optical scanner of a system for the separation of heterogeneous material configured in accordance with one embodiment of the present invention.
Figure 4:
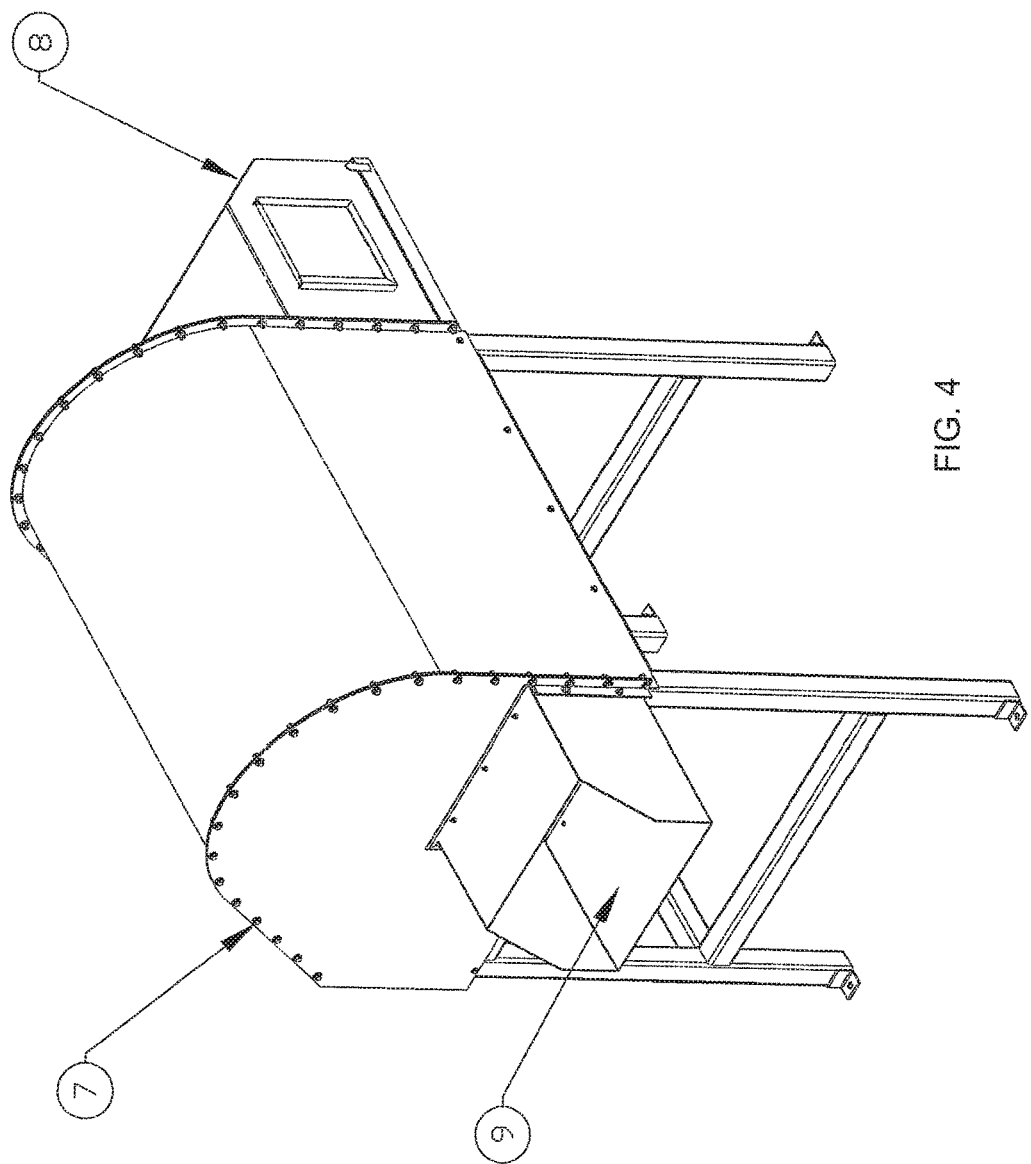
FIG. 4 is a side perspective drawing illustrating a blower hood configured for use in a system for the separation of heterogeneous material configured in accordance with one embodiment of the present invention.
Figure 5:
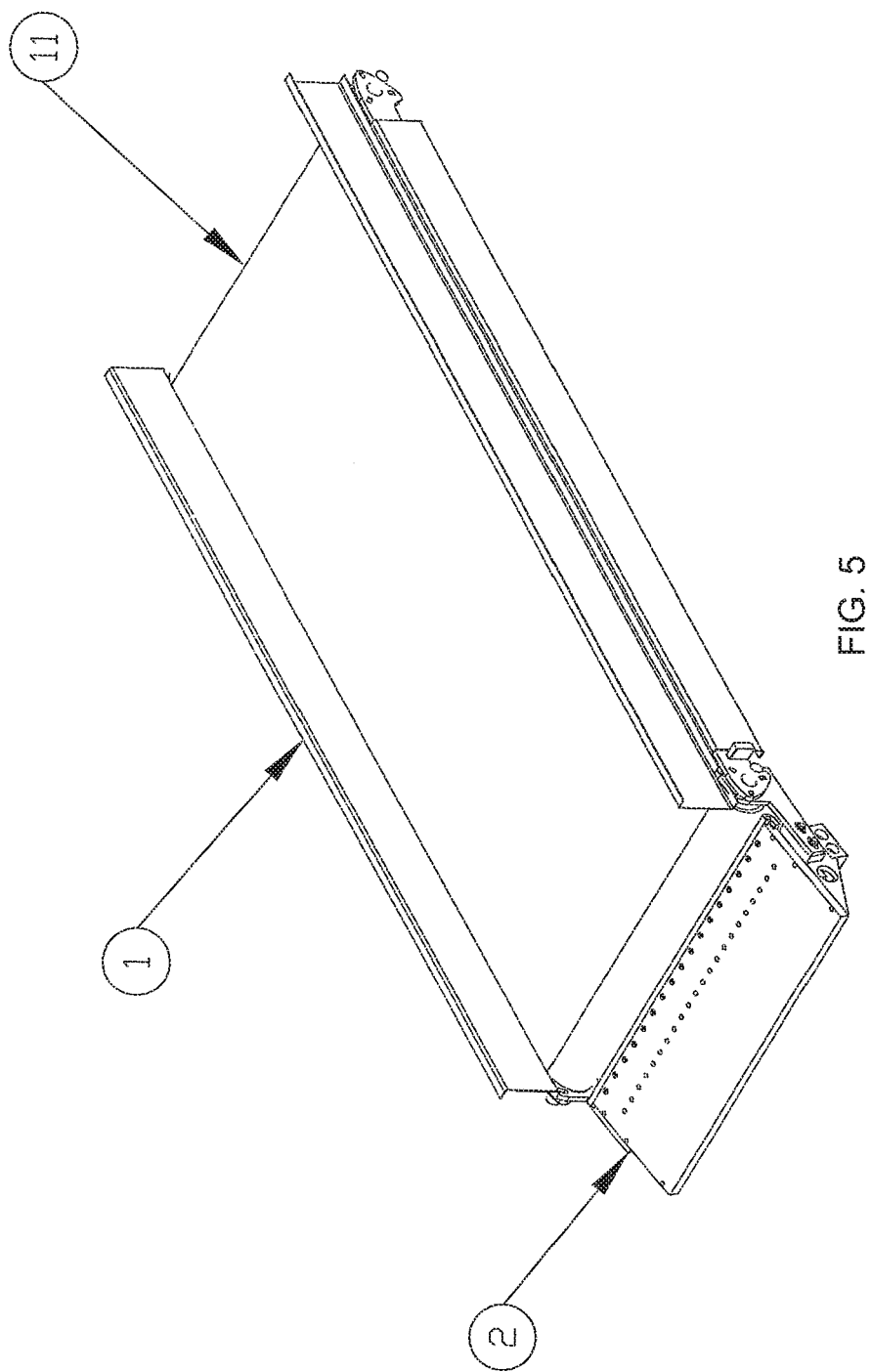
FIG. 5 is a front perspective drawing illustrating a conveyer, air knife and ejector configured for use in a system for the separation of heterogeneous material configured in accordance with one embodiment of the present invention.
Figure 6:
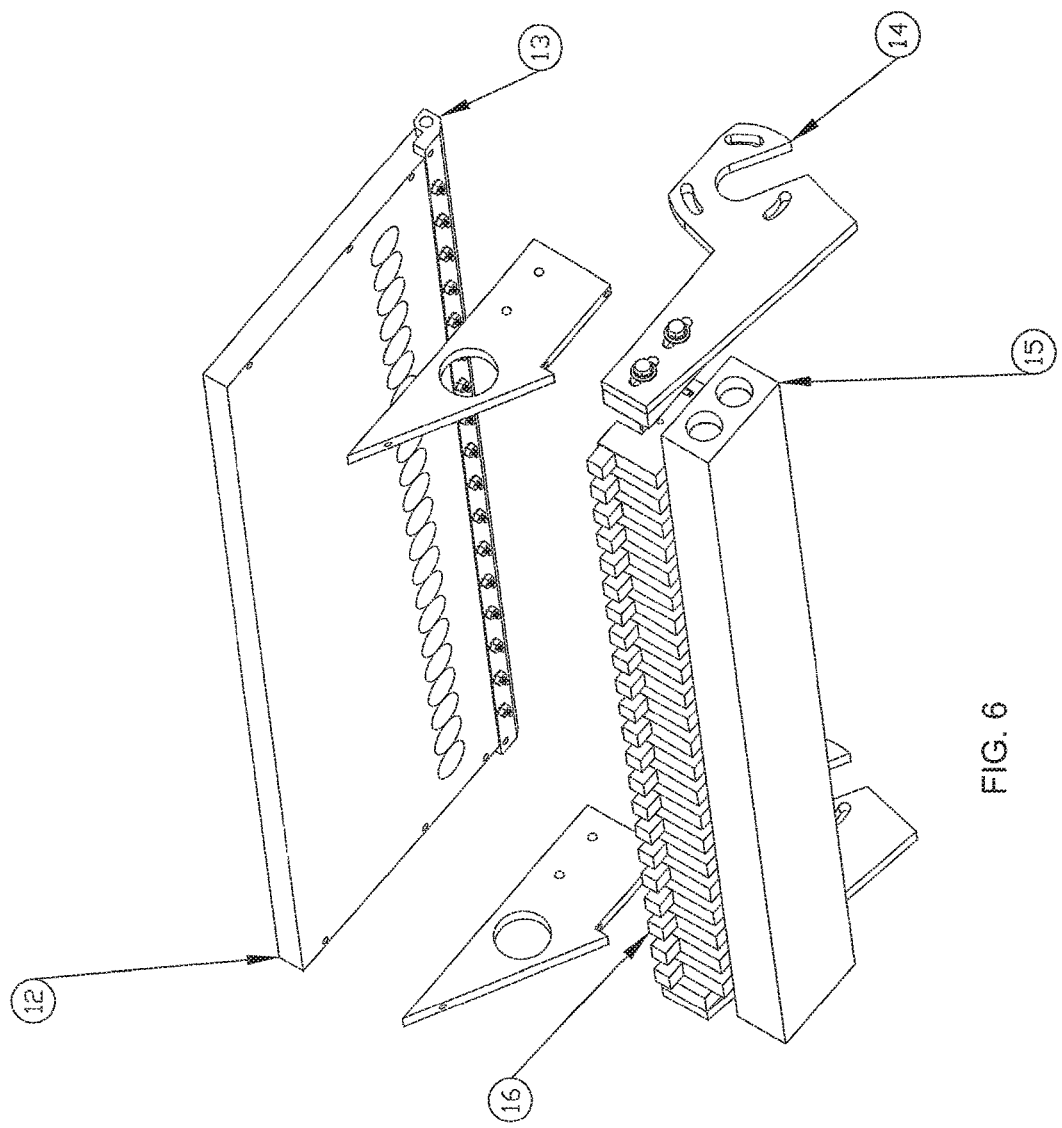
FIG. 6 is a bottom, exploded perspective drawing illustrating an air knife and ejector configured for use in a system for the separation of heterogeneous material configured in accordance with one embodiment of the present invention.
Figure 7:
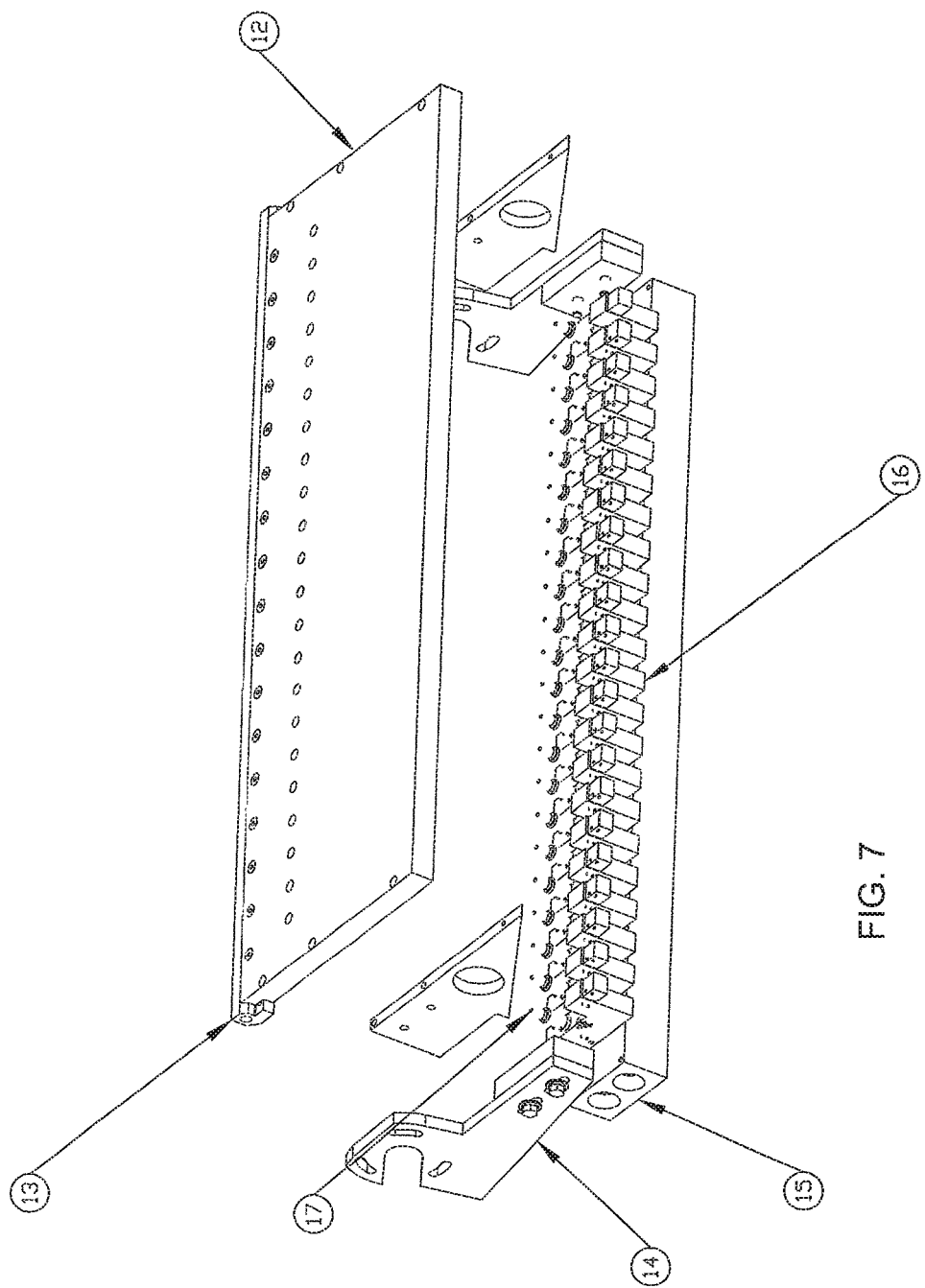
FIG. 7 is a top, exploded perspective drawing illustrating an air knife and ejector configured for use in a system for the separation of heterogeneous material configured in accordance with one embodiment of the present invention.

In one such embodiment, illustrated in FIGS. 1 and 2, a conveyer 1 carries material to a identification camera enclosure 4. The identification camera enclosure 4 encloses a camera 6 disposed proximately to an array of lights 5, highlighting the target area for the camera 6. In such a system, the camera 6 is a hyperspectral camera. Hyperspectral cameras and sensors such as those employed in the one embodiment of the present invention collect and then combine spatial and spectral information as a set of 'images'. In one embodiment, illustrated in FIG. 3, the camera 6 may be mounted on camera mounting brackets 10.

Each image, thus generated, represents a range of the electromagnetic spectrum and is also known as a spectral band. These 'images' are then combined and form a three dimensional hyperspectral cube for processing and analysis.

Hyperspectral sensors also referred to as "imaging spectroscopy" look at objects using a vast portion of the electromagnetic spectrum. Certain objects leave unique 'fingerprints' across the electromagnetic spectrum. These 'fingerprints' are known as spectral signatures and enable identification of the materials that make up a scanned object. Identification systems, can compare the spectral "fingerprint" of a sample with an unknown composition to a known spectra from a library of known exemplars.

Hyperspectral cameras of one embodiment of the present invention, utilize visible light, ultraviolet, and infrared spectral imaging that utilizes spatial information provided by the hyperspectral image. Infrared is, in such an embodiment, the primary band utilized in identifying individual recyclable commodities encompassing sometimes a variety of spectral signatures including color for sorting and commodity segregation purposes. One skilled in the art will appreciate that embodiments of the present invention may be used in sorting heterogeneous materials in other fields including but not limited to agriculture, medicine, and industrial applications.

Hyperspectral data, collected by the camera 6, comprises a set of contiguous bands. In one embodiment of the present invention, this is collected by a single sensor, interfaced with an ejection method that resides within its field of vision and then used to select the desired item. This is in contrast to conventional multispectral techniques, where a set of optimally chosen spectral bands that are typically not contiguous and need to be collected from multiple sensors. This collection of spectral data is valuable in improving the accuracy of the identification, and is employed in various embodiments of the present invention. A single sensor, in one embodiment of the present invention, performs all the following tasks: Identify items searched for in a large area; searching for multiple items at the same time; identifying items by composition and color all with a higher degree of positive identification. Thus a single system may be programmed to sort all commodities required by a user.

One embodiment of the present invention provides a system equipped with Wedge Jet style high flow ejection air nozzles 17 and high speed real time computer interfaces thus providing an ejection method capable of propelling desired items into an elevated air conveyance system enabling multiple units to be orientated on a straight line.

A straight line orientation enables optical sorting systems to be installed in a smaller area with no vertical grade differential, thus enabling the simple retrofit of existing manual sorting lines with optical automatic sorters with minimal site work. Such an embodiment also enables new systems to be engineered into a much smaller footprint than existing traditional saw tooth designs which require elevation consideration. A system design configured according to one embodiment of the present invention and illustrated in FIGS. 1 and 2 provides an accelerator rubber belt feed conveyor 1 of varying widths traveling at a rate of between 200 to 600 feet per minute. A light bar system 5 shines a high intensity light down on the belt where the hyperspectral imaging camera 6 collects its data. The camera 6 collects that data and feeds a high speed Lenox computer system or other suitable computer system 3 that has been programmed to receive this data and then provide output signals timed with the ejector nozzles 17 to eject desired product. Immediately after the discharge of the accelerator conveyor 1 is disposed an air knife 2 that helps to levitate materials and decreases the likelihood of material lodging between the accelerator belt 1 and manifold ejector plate 14. The manifold ejection plate 12 houses the wedge jets 17 and enables those jets 17 to be directed to optimal lift. The wedge jets 17 also referred to as vortex, Typhoon, Hurricane or Fixed Flow Air Nozzles are fast acting, resistant to plugging and deliver a high velocity directed air flow that then expands to an 8" diameter air flow. A venturie effect delivered by this style ejection jet positively holds the ejected item within its air flow decreasing the likelihood of the item colliding with competitive items in the air and discouraging turbulence. The additional force generated by these jets 17 propels the picked items into a receiving hood 7 area located above the accelerator belt 1. This receiving hood system 7 is fitted with a high velocity fan type blower 8 that then pushes the selected items toward the collection point 9 at a 90 degree angle. In an alternative embodiment, the ejection system can be configured with at least one flipping lever or other mechanical device whereby desired material is pushed or otherwise segregated. Negative materials not selected continue down the ejector plate 12 and are deposited on another accelerator conveyor (not shown) upon which non-selected materials move in series to additional optical system where another desired item can be sorted and removed from the waste stream. In such an embodiment, each optical sorter may be deployed in line with the previous sorter in a very tight configuration with no change in elevation. The evacuation fan within the collection hood also develops a venture effect that helps to draw light fractional items into its air stream enhancing the collection rate of ejected selected items. An evacuation conveyor could also be positioned in this location and would deliver similar results.

A further embodiment provides an accelerator conveyor enabling the spreading out of materials, a hyperspectral imaging camera designed to positively identify about approximately 100% of the desired item (for example, a recyclable material or other component of a heterogeneous material), items, air nozzle cannons with fast acting solenoid air valves which react to information provided by imaging camera designed to lift desired fractional recyclable material.

Yet another embodiment provides an air conveyance system which develops a Venturi effect drawing in the previously lifted desired items and evacuating those items to a holding bin.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A system for the identification and sorting of heterogeneous material, the system comprising:

a hyperspectral identification system for capturing spectra of material, said hyperspectral identification system comprises at least one hyperspectral camera said hyperspectral camera receiving a plurality of selected spectral bands of infrared and visible light corresponding to spectral signatures of target materials to be identified if present in said heterogeneous material; said camera capturing hyperspectral images comprising spectral and spatial data for articles within said heterogeneous material; said camera disposed proximate to a visible or infrared light source, said light source and said at least one hyperspectral camera are disposed on the same side of a stream of said heterogeneous material;

a solid belt having first and second ends, said belt running beneath said hyperspectral identification system and upon which said heterogeneous material is conveyed from said first end to said second end, said belt traveling at a preset rate, said hyperspectral identification system being disposed over said second end of said belt;

a computer receiving and analyzing data from said hyperspectral identification system and selecting materials of a first user defined category from said materials; and an ejection system disposed immediately after said second end of said belt, whereby said desired materials are separated from said heterogeneous material, said ejection system being triggered by said computer at a preset time delay equal to the distance between said camera and said ejection system divided by the rate of travel of the belt.

2. The system according to claim 1, further comprising a conveyer to deliver said heterogeneous material to said system.

3. The system according to claim 1 further comprising a receiving system, whereby said materials of a first user defined category are segregated and collected.

4. The system according to claim 1 wherein said hyperspectral identification system is configured to collect spectral and spatial information from heterogeneous material entering said system and store said spectral and spatial information as images.

5. The system according to claim 1 wherein said ejection system comprises a plurality of independently controlled air nozzles disposed beneath said material, and a blower hood disposed above said material, said blower hood providing an air current whereby said selected material is blown out of a discharge port.

6. The system according to claim 1 wherein said heterogeneous materials comprise waste and recyclable materials.

7. The system according to claim 1 wherein said computer can select a plurality of user defined materials.

8. The system according to claim 1 wherein said ejection system comprises a mechanical ejector.

9. The system according to claim 1 further comprising an array of lights disposed proximate to said hyperspectral identification system.

10. The system according to claim 9 wherein said lights have a wavelength suitable for hyperspectral imaging.

11. The system according to claim 9 wherein said computer comprises software configured to compare said images to images stored in a library of images.

12. The system according to claim 1 wherein said ejection system comprises a fluid jet.

13. The system according to claim 12 wherein said fluid jet is a water jet.

14. A method for sorting heterogeneous material, said method comprising:

reflecting visible or infrared light from the surface of said heterogeneous material disposed on a conveyer;

conveying said heterogeneous material at a predetermined rate through a hyperspectral imager;

generating hyperspectral images of said heterogeneous material comprising spectral and spatial data for articles within said heterogeneous material by receiving a plurality of selected spectral bands of infrared and visible light corresponding to spectral signatures of target materials to be identified if present in said heterogeneous material as said heterogeneous material passes on said conveyer beneath said hyperspectral imaginer;

comparing said hyperspectral images of said heterogeneous material to hyperspectral images of known materials;

identifying said target materials;

after a preset time interval from said identifying said target material, said interval equal to the distance between said hyperspectral imager and a separating system divided by the predetermined rate, physically isolating target material from said heterogeneous material by separating said target material from said heterogeneous material as it leaves said conveyer immediately after said hyperspectral imager.

15. The method according to claim 14 wherein said heterogeneous material comprises waste material and recyclable material in combination.

* * * * *